(12) United States Patent
Hoffman et al.

(10) Patent No.: US 8,924,224 B2
(45) Date of Patent: Dec. 30, 2014

(54) SYSTEM AND METHOD FOR CREATING AND DISPLAYING OPTIONAL ORDER SETS IN HEALTHCARE ENVIRONMENT

(75) Inventors: Mark A. Hoffman, Lees Summit, MO (US); Scott M. Haven, Pleasant Valley, MO (US); Ginger H. Kuhns, Liberty, MO (US); Kevin M. Power, Pleasant Valley, MO (US)

(73) Assignee: Cerner Innovation, Inc., Kansas City, Kansas, MO (US)

( * ) Notice: Subject to any disclaimer, the term of this patent is extended or adjusted under 35 U.S.C. 154(b) by 1380 days.

(21) Appl. No.: 11/537,924

(22) Filed: Oct. 2, 2006

(65) Prior Publication Data

US 2007/0088578 A1    Apr. 19, 2007

Related U.S. Application Data

(60) Provisional application No. 60/722,481, filed on Sep. 30, 2005.

(51) Int. Cl.
| | | |
|---|---|---|
| *G06Q 50/00* | (2012.01) | |
| *G06Q 30/06* | (2012.01) | |
| *G06F 19/00* | (2011.01) | |

(52) U.S. Cl.
CPC ........... *G06Q 30/06* (2013.01); *G60Q 50/24* (2013.01); *G06F 19/3456* (2013.01)
USPC ................................ 705/2; 705/3; 600/300

(58) Field of Classification Search
CPC ... G06Q 50/22; G06Q 50/24; G06Q 19/3456; G06Q 19/345; G06Q 19/363; G06Q 19/325
USPC .......................................... 705/2–3; 600/300
See application file for complete search history.

(56) References Cited

U.S. PATENT DOCUMENTS

| | | | | |
|---|---|---|---|---|
| 5,723,293 | A * | 3/1998 | Huang | 435/6 |
| 5,823,948 | A * | 10/1998 | Ross et al. | 600/300 |
| 5,991,728 | A * | 11/1999 | DeBusk et al. | 705/2 |
| 2002/0047905 | A1* | 4/2002 | Kinjo | 348/207 |
| 2002/0143572 | A1* | 10/2002 | Akagi | 705/1 |
| 2003/0074220 | A1* | 4/2003 | Brandt | 705/2 |
| 2005/0015279 | A1* | 1/2005 | Rucker | 705/2 |
| 2006/0136260 | A1* | 6/2006 | Ash et al. | 705/2 |
| 2006/0136261 | A1* | 6/2006 | Ash et al. | 705/2 |
| 2006/0136268 | A1* | 6/2006 | Ash et al. | 705/3 |
| 2006/0149416 | A1* | 7/2006 | Mohapatra et al. | 700/242 |
| 2006/0173710 | A1* | 8/2006 | Komischke | 705/2 |
| 2006/0277070 | A1* | 12/2006 | Hungerford et al. | 705/3 |

* cited by examiner

*Primary Examiner* — Sind Phongsvirajati
(74) *Attorney, Agent, or Firm* — Shook, Hardy & Bacon LLP (57) ABSTRACT

A method, system and computerized medium in a computerized environment for placing optional orders for an order set for a patient is provided. A request to display an order set for a patient is received. The order set comprises one or more optional orders. The optional orders that may or may not be placed for the order set. The optional orders are determined and the optional orders are displayed. A selection of one or more of the optional orders to be placed for the order set is received and the selected optional orders are placed for the order set.

7 Claims, 11 Drawing Sheets

SYSTEM AND METHOD FOR CREATING AND DISPLAYING OPTIONAL ORDER SETS IN HEALTHCARE ENVIRONMENT

CROSS-REFERENCE TO RELATED APPLICATIONS

This application claims the benefit of priority to U.S. Provisional Application Ser. No. 60/722,481 filed on Sep. 30, 2005.

STATEMENT REGARDING FEDERALLY SPONSORED RESEARCH OR DEVELOPMENT

Not applicable.

BACKGROUND

A healthcare order in a clinical information system represents a request by a caregiver for an action related to the patient. The action may be at the initiation of a diagnostic test, the administration of medication, or any other of a variety of other healthcare activities. Orders are captured by a clinical information system in a variety of ways including direct user entry through a computerized provider order entry (CPOE) or indirect entry by an intermediary, for example a verbal or written request received from a doctor and entered by a user of the system, or by receiving an order from an interface from another information system. Orders may be placed singly or as a group of orders. A single order may include ordering an individual medication or laboratory test for a patient, while an order set includes multiple orders for a patient. An exemplary order set is a Chem 20 laboratory test, which includes a panel of discrete tests that are ordered through a single ordering action.

Often, when performing primary clinical processes, there are limited subsets of related orders that may be appropriate under certain circumstances. In existing systems, a user is required to either place all possible orders for an order set and then cancel any orders later deemed unnecessary due to the circumstances, or to place each order individually at one or more points in time. However, these approaches are time consuming and interrupt a caregiver's workflow. It would be beneficial to have a system and method associate a set of appropriate orders in a manner that permits a user to easily select only those needed in a specific instance.

SUMMARY

One embodiment of the present invention relates to a method in a computerized environment for displaying optional healthcare orders. A healthcare order set for a patient is accessed. The order set includes a first optional order and a second optional order, where the first and second optional orders may or may not be selected to be placed. The first optional order is displayed before the order set has been placed. A request to place the order set is received and the second optional order is displayed after the order set has been placed.

In another embodiment, a method in a computerized environment for placing optional orders for an order set for a patient is shown. A request to display an order set for a patient is received. The order set comprises one or more optional orders. The optional orders that may or may not be placed for the order set are determined and the optional orders are displayed. A selection of one or more of the optional orders to be placed for the order set is received and the selected optional orders are placed for the order set.

In yet another embodiment, a computerized system for displaying optional healthcare orders is provided. The system comprises an accessing component for accessing a healthcare order set for a patient. The order set comprises a first optional order and a second optional order, where the first and second optional orders may or may not be selected to be placed. The system further comprises a first displaying component for displaying the first optional order before the order set has been placed and a receiving component for receiving a request to place the order set. The system comprises a second displaying component for displaying the second optional order after the order set has been placed.

In still another embodiment of the present invention, a system in a computerized environment for placing optional orders for an order set for a patient is provided. The system comprises a first receiving component for receiving a request to display an order set for a patient. The order set comprises one or more optional orders. The system further comprises a determining component for determining the optional orders that may be placed for the order set and a displaying component for displaying the optional orders to be selected to be placed. The system includes a second receiving component for receiving a selection of one or more of the optional orders to be placed for the order set and an ordering component for placing the selected optional orders for the order set.

BRIEF DESCRIPTION OF THE SEVERAL VIEWS OF THE DRAWINGS

The present invention is described in detail below with reference to the attached drawing figures, wherein.

DETAILED DESCRIPTION

In one embodiment of the present invention, optional healthcare orders are associated with a set of healthcare orders. The optional orders may be activated when the order set is placed, allowing them to have information captured in a computerized healthcare information system for the order. Optional orders may be activated at a variety of times; including when the order set is first placed or subsequently based on clinical information determined during the workflow. Optional orders allow for the flexibility of placing only those orders which are initially requested without having to cancel orders that are not needed, or building a different set of orders for every possible combination of orders that could be requested throughout the process.

An order in a clinical information system represents a request by a clinician for an action related to the patient. The action can be the initiation of a diagnostic test, the administration of a medication any of a number of other actions or tasks. Orders are captured by clinical information systems by a variety of means—direct user entry (Computerized Provider Order Entry (CPOE)), indirect entry by an intermediary, for example a verbal or written request that is conveyed to a nurse, lab technologist or pharmacist; or by an interface from another information system.

Orders can be placed singly or as a set. An example of a single order would be ordering an individual medication or a serology test, while an order set includes multiple orders. An exemplary order set is a Chem 20, in which a number of discrete laboratory tests are ordered through a single action. Placing an order in the system has a variety of implications, including its formal presence in the clinical workflow and the triggering of other billing-related and clinical events.

In one embodiment of the invention, an order within a set of orders can be designated as optional. Unlike conventional orders, optional orders are not placed in the system by default when the set of orders is placed. An optional order can be activated at the time the order set is placed or later in the clinical process. If the user is ordering a set of orders associated with optional orders, the user is prompted to activate the optional orders. Optional orders that are selected are activated and added to the set of orders. Optional orders that are not activated when ordering the order set are displayed with the set of placed orders, allowing the optional orders to be activated later, if necessary. A technologist or other user can activate optional orders based on the findings associated with other orders in the case, allowing for flexibility of the testing path. In another embodiment, the ability is provided to designate whether the activation of the order can occur at order time or only after the set of orders have been placed.

Figure 1:
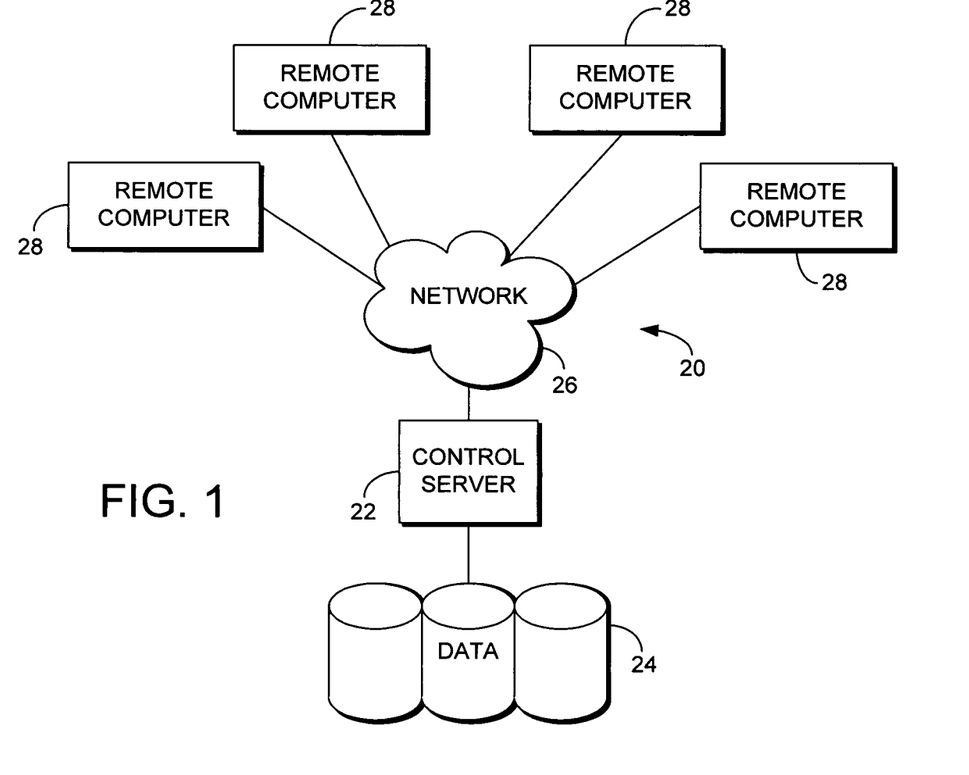
FIG. 1 is a block diagram illustrating a system for use in accordance with an embodiment of the invention.

With reference to FIG. 1, an exemplary medical information system for implementing the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technologists, physician's assistants, nurse practitioners, nurses, nurse's aides, pharmacists, dieticians, microbiologists, laboratory experts, laboratory scientist, laboratory technologists, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a windows operating system operating in conjunction with a LAN operating system, one skilled in the art would recognize that the method and system can be implemented in any system.

Figure 2:
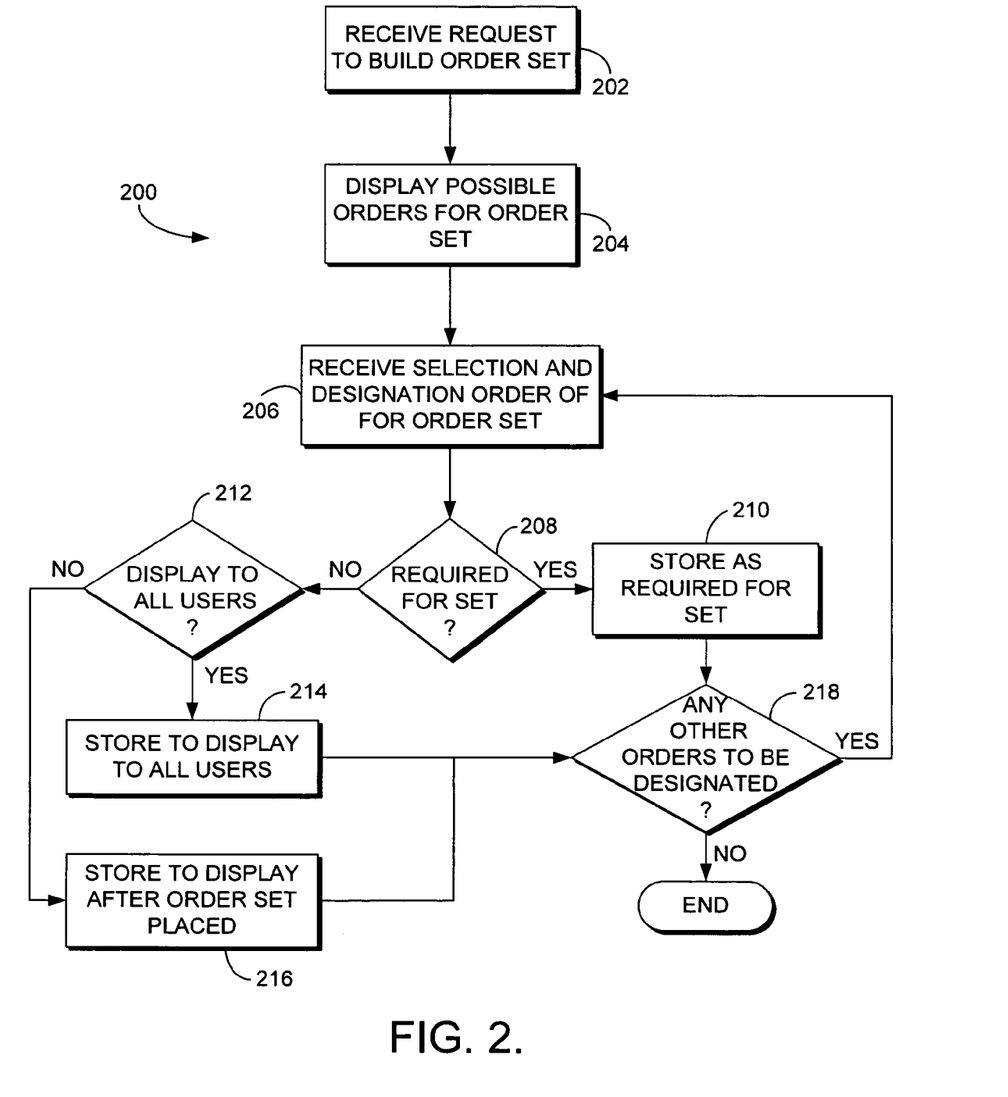
FIG. 2 is a flow diagram illustrating a method for configuring and storing designations of possible healthcare orders in order sets in accordance with an embodiment of the present invention.

With reference to FIG. 2, a method 200 in a computerized healthcare environment for configuring storing designations of orders in order sets is shown. At step 202, a request to build an order set is received. A database is accessed and possible orders for the specified order set are displayed at step 204. A user may select orders from a list of possible orders to construct an order set. Each order selected for the order set is designated as optional or required for the order set. The designation of a selected order is received at step 206 of FIG. 2. At step 208, it is determined whether the selected order has been designated as required for the order set. If the order is required at step 210, the selected order is stored in a table or database as a required order for the order set. An exemplary database is a relational database computer system in which orders for testing can be placed. Alternative databases could include XML documents or an object oriented database integrated with a clinical information system.

If at step 208 it is determined that the selected order is not required for the order set at step 212, it is determined whether the order has been designated to be displayed to all users. An order designated to be displayed to all users may be activated by a caregiver placing the order set. The order also may be displayed to a laboratory scientist or technologist after the order set has been placed. A technologist or scientist may activate optional orders not activated by the caregiver when the order set was originally placed based on laboratory findings associated with other orders in the set. In some instances, the presence or absence of additional data available to the technologist that was unavailable to the caregiver at the time the order set was placed may be used to determine if the optional orders should be activated.

If the order has been designated to be displayed to all users at step 214, the order is stored as being an optional order that is displayed to all users of the system. If at decision step 212 it is determined that the order is not to be displayed to all users, at step 216 it is stored that the order is to be displayed only after the order set is initially ordered. For example, the order may be selected to be displayed as optional after the order set has been placed so that a laboratory scientist or technician can view the optional order but not displayed to a caregiver placing the initial order set. At step 218, it is determined whether there are any other orders for the order set to be designated to be part of the order set. If so, at step 206 the selection and designation of another order for the order set is received.

Figure 6:
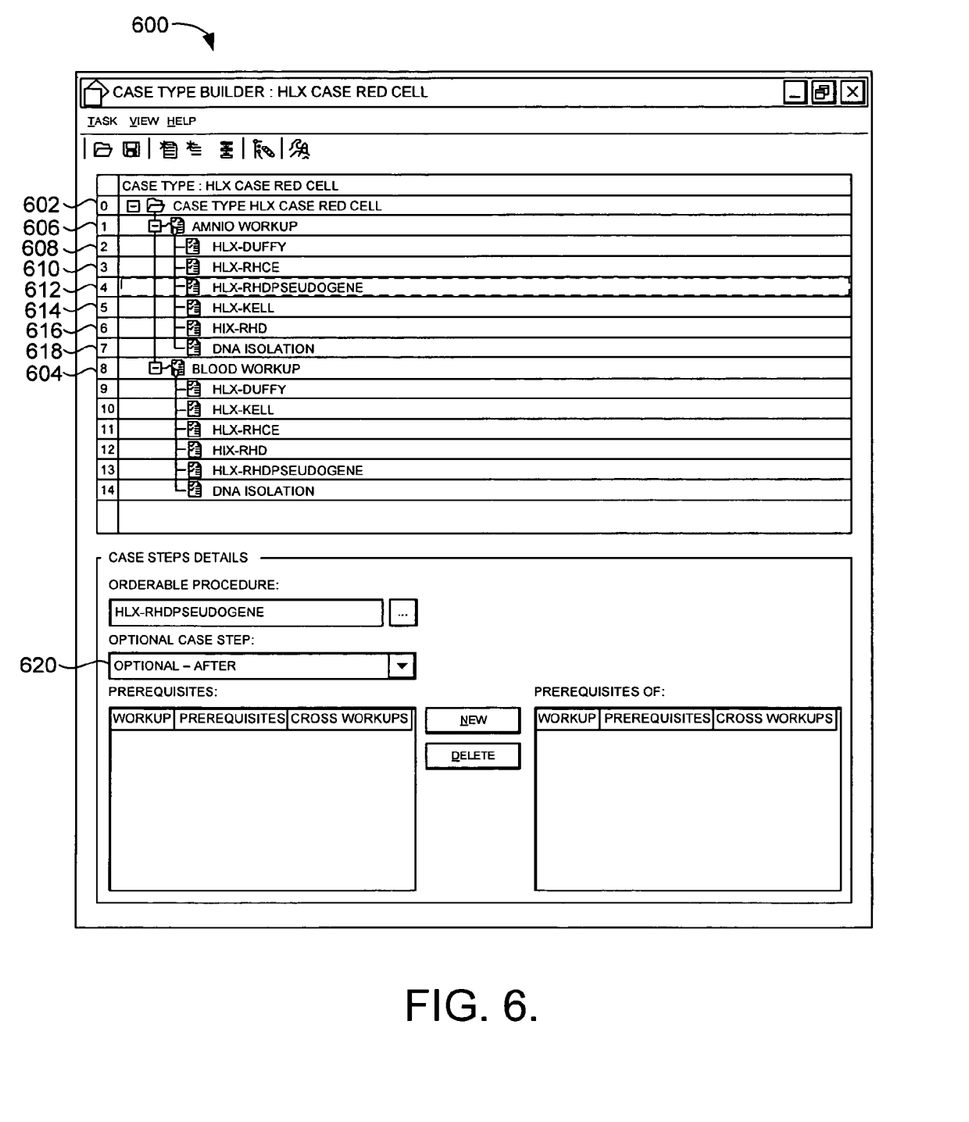
FIG. 6 is a screen displaying how an order within an order set being defined and built as an optional in accordance with an embodiment of the present invention in order to be displayed to a second used after the order set has been placed.

For example, with reference to FIG. 6, the screen 600 displays building an order set for a healthcare environment. The order set is for a case type HLX case red cell 602. The case type may also be organized into sample and specimen types such as amniotic fluid 606 or a blood 604. For the amniotic fluid 606 there are six possible orders for the HLX red cell 602 order set. The possible orders include an HLX-Duffy order 608, an HLX-RHCE order 610, an HLX-RHD pseudo gene order 612, an HLX-Kell order 614, and HLX-RHD order 616 and a DNA isolation order 618. In screen 600, the HLX-RHD pseudo gene order 612 is designated as an optional order for the order set to be displayed only after the initial order set for the patient has been placed by selecting dropdown menu item 620. As such, the order will only be displayed to a designated laboratory user fulfilling orders from the order set and not to the caregiver placing the initial order set.

Figure 7:
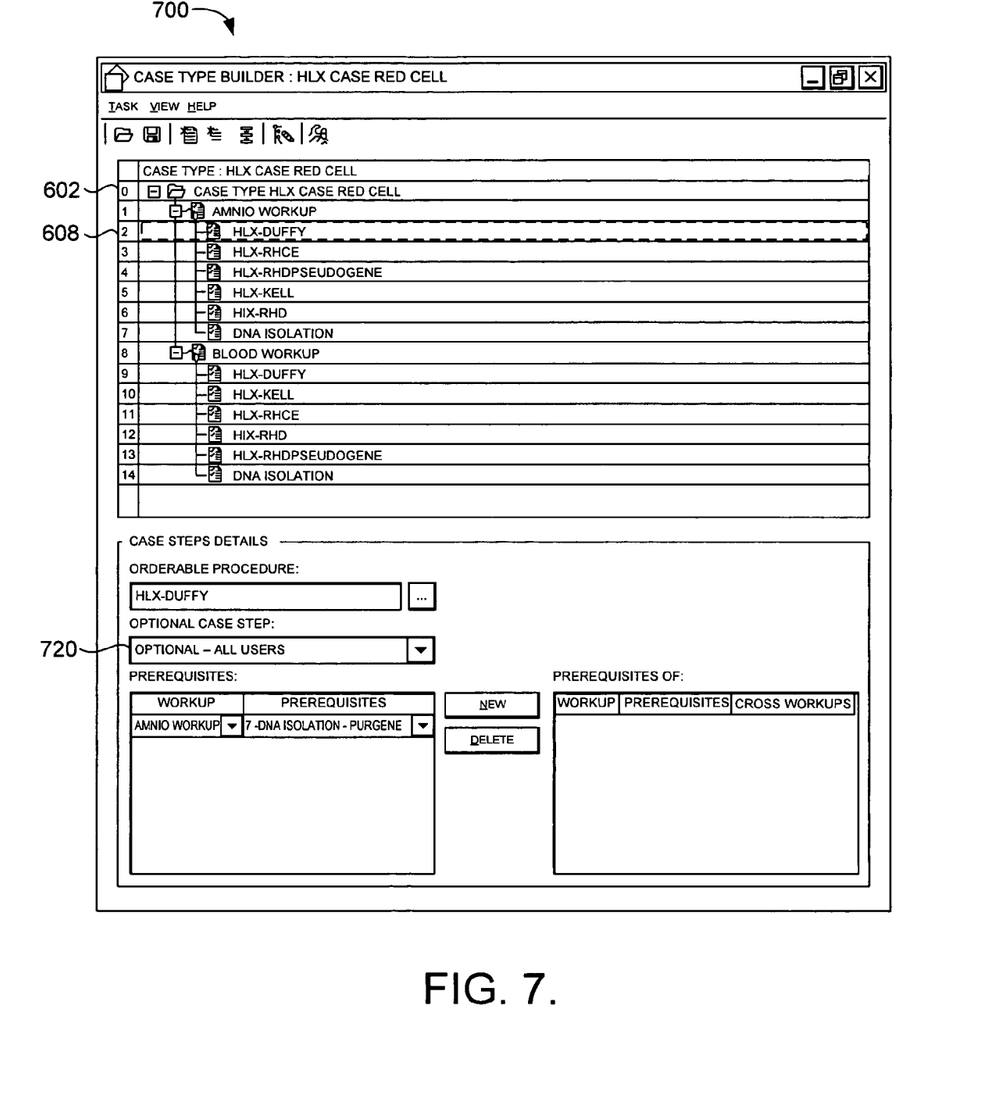
FIG. 7 is a screen displaying how an order within an order set may be defined and built as optional order to be displayed to all users in accordance with an embodiment of the present invention.

With reference to FIG. 7, a screen 700 is shown displaying possible orders for the order set 602 for the case type HLX case red cell for amniotic fluid. In this example, the order HLX-Duffy 608 is designated as an optional order for the order set to be displayed to all users by selecting dropdown menu item 720. Thus, the optional order of HLX-Duffy will be displayed as an optional order for the order set to all users including the initial caregivers and laboratory users.

Figure 8:
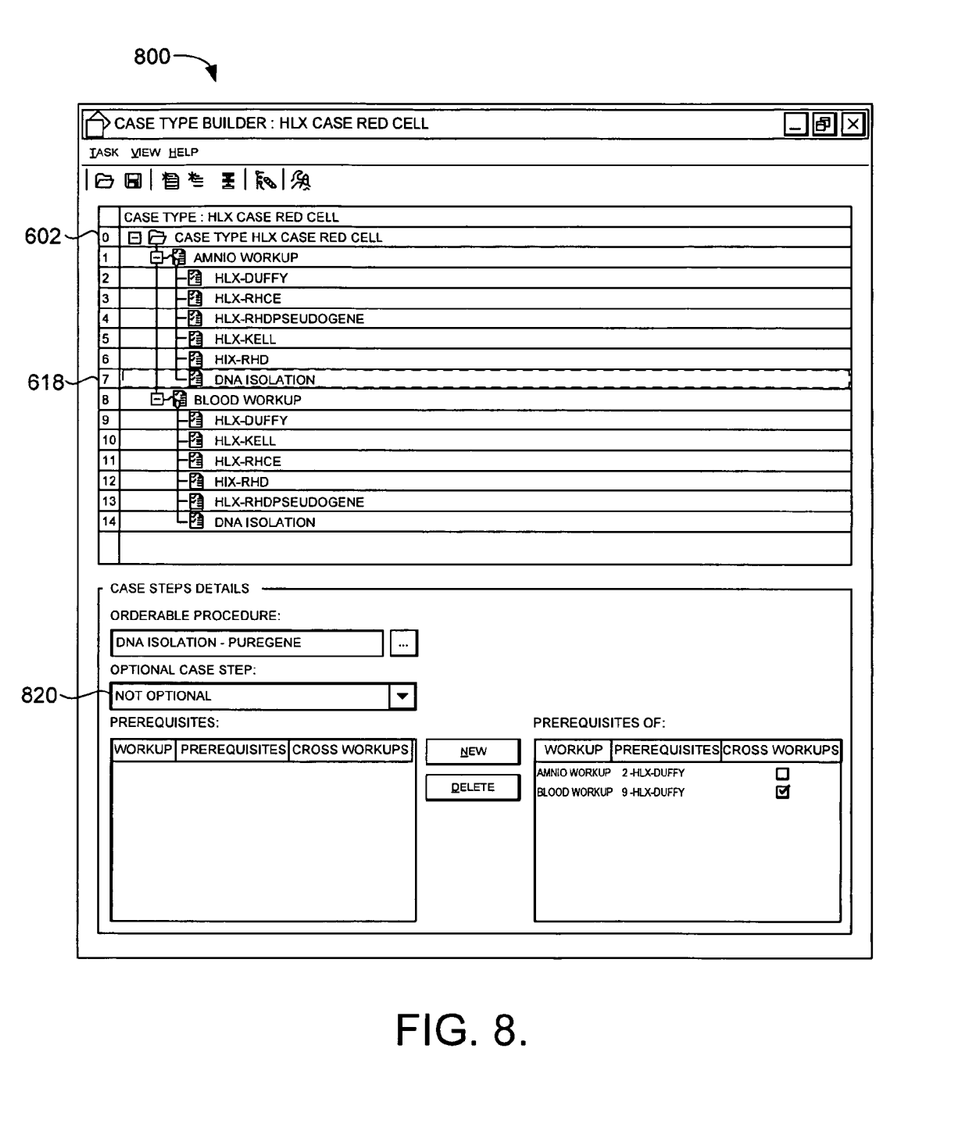
FIG. 8 is screen displaying how an order within an order set may be defined and built as being required for the order set in accordance with an embodiment of the present invention.

With reference to FIG. 8, a screen is shown for building the case type HLX case red cell 602 for amniotic fluid. In this example, the DNA isolation order 618 is being designated as "not optional" by selecting dropdown menu item 820. Thus, the order of DNA isolation will be included in the order set, however, it will not capable of being selected by a user. It will be required each and every time the order set is placed.

Figure 3:
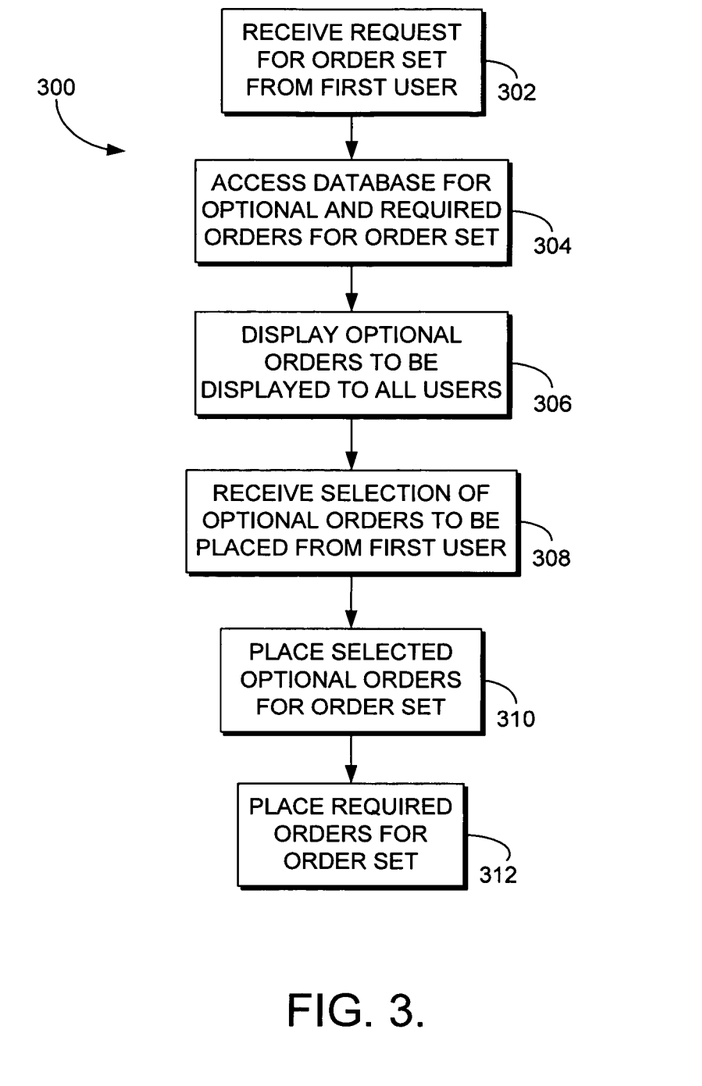
FIG. 3 is a flow diagram illustrating a method for receiving the selection of optional orders from an order set to be placed from a first user in accordance with an embodiment of the present invention.

With reference to FIG. 3, a method 300 for receiving the selection of optional orders from an order set and placing the optional orders is shown. At step 302, a request for an order set to be placed is received from a first user. The first user may be a caregiver responsible for placing the initial order set for a patient. At step 304, a database is accessed to determine the optional and required orders for the order set. The accessed database may be built using the steps described in FIG. 2.

Figure 9:
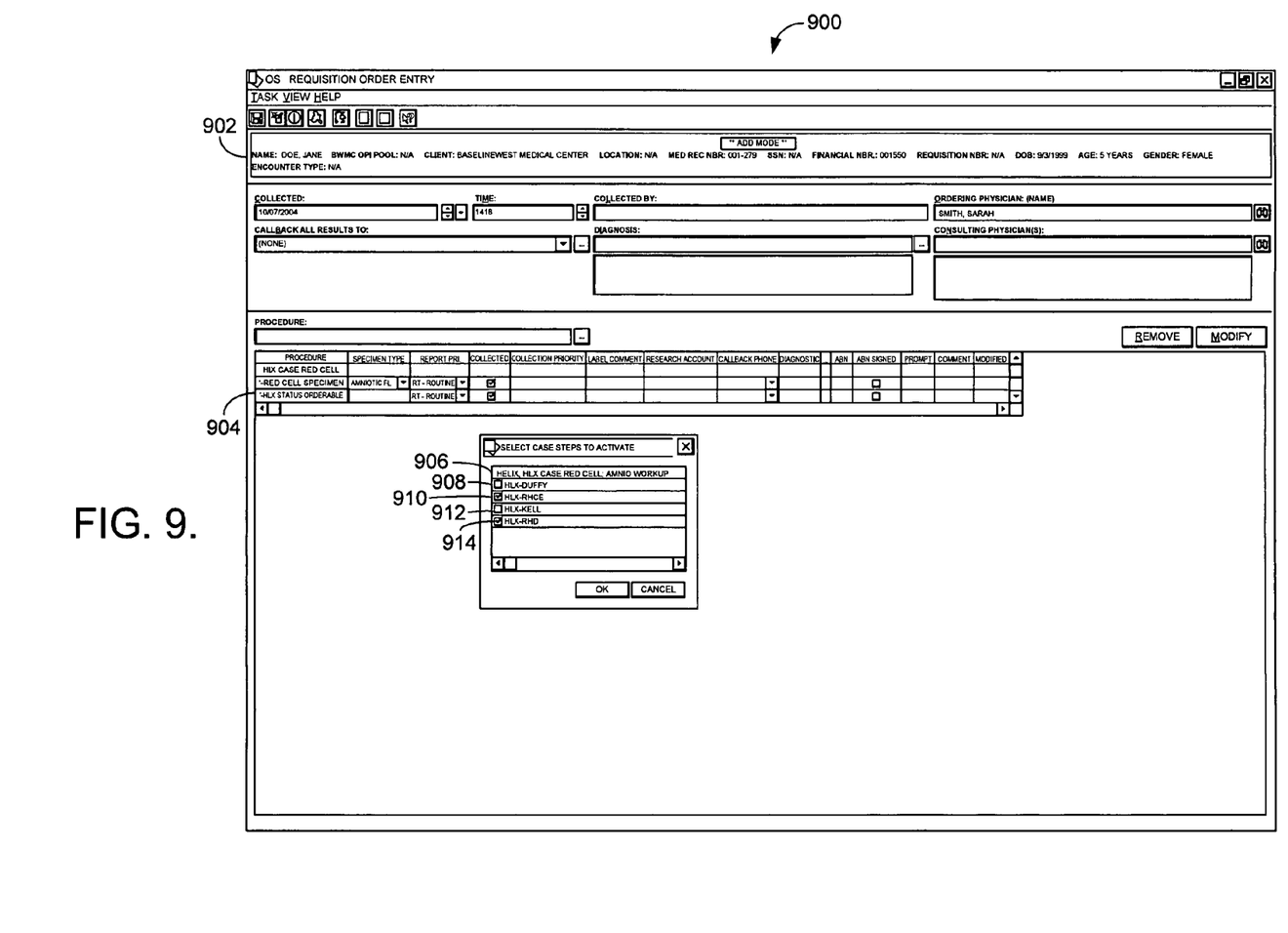
FIG. 9 is a screen displaying how optional orders may be activated when an order set is ordered in accordance with an embodiment of the present invention.

At step 306 of FIG. 3, optional orders to be displayed to all users are displayed. Specifically, the optional orders designated to be viewed by all users at step 214 of FIG. 2 are displayed to the user placing the initial order set. The caregiver may be a healthcare provider, such as a nurse or doctor. With reference to FIG. 9, a screen 900 displaying the manner in which optional orders may be activated is shown. In this example, optional orders for fictitious patient Jane Doe 902 are displayed. The optional orders from which a caregiver may choose in the HLX cell order set 904 are the HLX-Duffy 906 order, the HLX-RHCE order 908, the HLX-Kell 912 order, and the HLX-RHD 914 order. These may be manually selected by a user or may be designated as pre-selected optional orders for that type of order set.

Referring again to FIG. 3, at step 308 selection(s) of optional orders to be placed by the user are received. Referring again to FIG. 9, in this example a user has selected the HLX-RHCE order 910 and HLX-RHD order 914 to be placed for the order set. The HLX-Duffy order 908 and the HLX-Kell order 912 are not selected from the list of optional orders and will not be placed.

Referring again to FIG. 3, at step 310 the selected optional orders are placed for the order set for the patient. At step 312, the orders that were designated as required are also placed for the order set for the patient.

Figure 4:
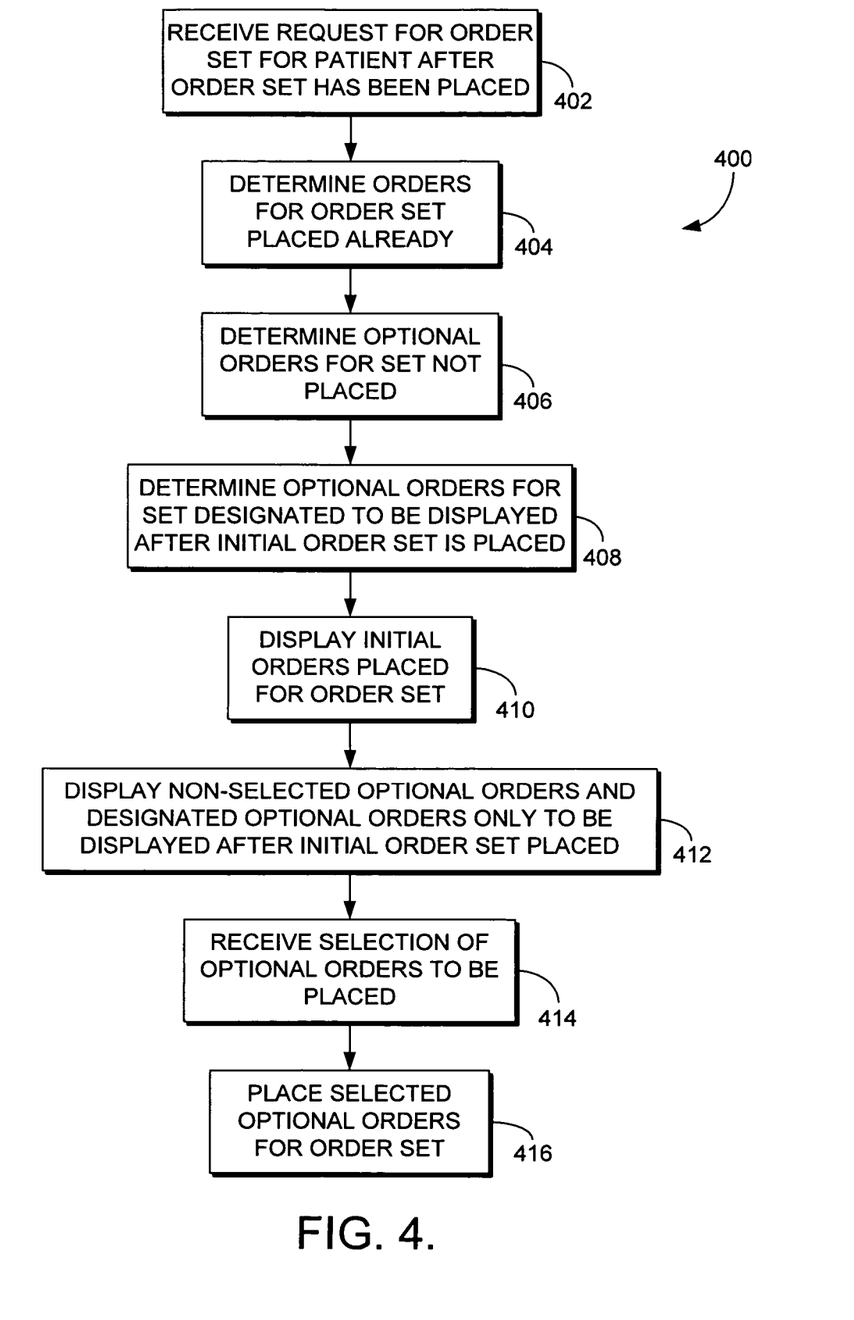
FIG. 4 is a flow diagram illustrating a method for receiving the selected optional orders to be placed by a second user in accordance with an embodiment of the present invention.

With reference to FIG. 4, a method 400 for displaying optional orders after the order set has been placed is shown. At step 402, a request is received for an order set after the order set has been previously placed. In one embodiment, a second user, such as a laboratory scientist or technologist fulfilling laboratory orders, requests to view the order set placed. At step 404, the orders placed for the order set are determined. A database or table that includes the orders placed for the order set for the patient is accessed. The database or table includes the optional orders selected by the first user. At step 406, it is determined which optional orders for the order set were not selected by a first user. Again, this information may be contained in a database or table.

At step 408, optional orders for the order set that were designated to be displayed only after the initial order set is placed are determined. At step 410, orders placed for the initial order set placed are displayed. These may be laboratory orders placed and to be fulfilled. At step 412, optional orders that were initially not placed for the order set are displayed and may be selected. Also at step 412, optional orders only to be displayed after the initial order set is placed are displayed. At step 414, the selection of optional orders to be placed is received. For example, a second user such as a laboratory technologist or scientist may select the optional orders to be placed. At step 416, the optional orders selected are placed for the order set.

Figure 5:
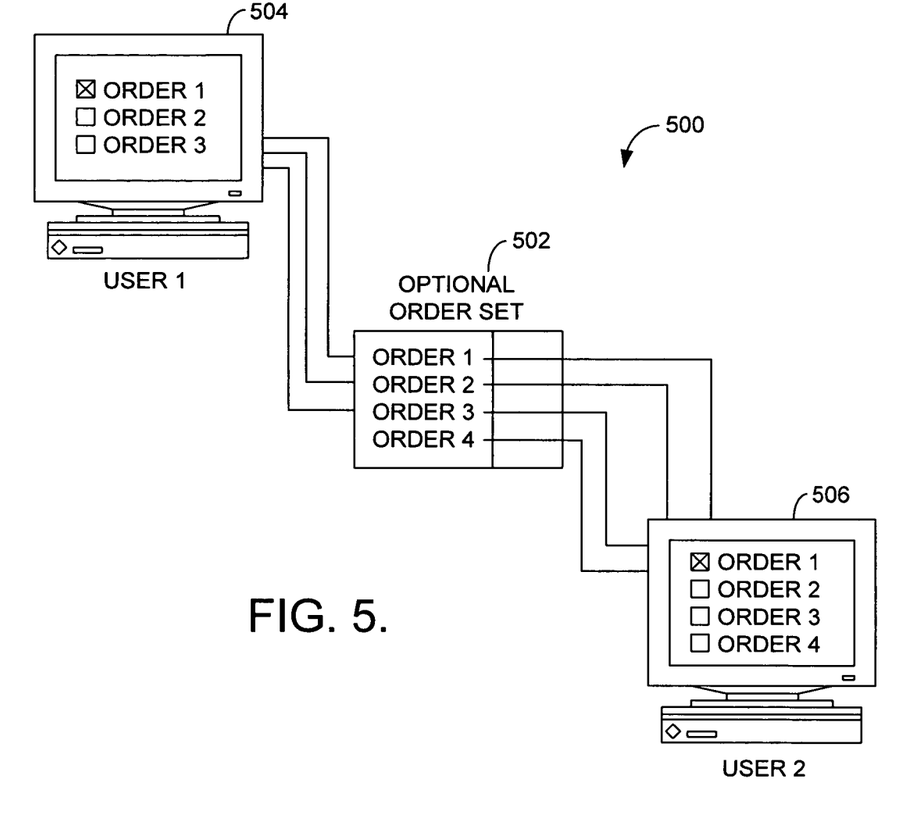
FIG. 5 is a diagram illustrating orders in an optional order set displayed to a first and second user in accordance with an embodiment of the present invention.

With reference to FIG. 5, a block diagram 500 displaying an exemplary optional order set 502 is shown. The optional order set 502 includes ORDER 1, ORDER 2, ORDER 3 and ORDER 4. ORDERS 1, 2 and 3 are designated to be displayed to all users. ORDER 4 is designated to be displayed only after the initial order set is placed. As such, optional orders 1, 2 and 3 are displayed to the first user 504 who is placing the initial order set.

The first user 504 has selected optional order 1 to be placed. As such, order 1 is displayed to the second user 506 as having been placed by the first user 504. As the initial order set has been placed by user 1, ORDERS 2 and 3 are displayed as optional to user 2 orders because ORDERS 2 and 3 were not placed by user 1. Optional order 4 is only displayed to user 2 as the initial order set has been placed by user 1. While this example expressed as having different users, it is possible that a single user who places the order may see different options depending on the point in the clinical process.

Figure 10:
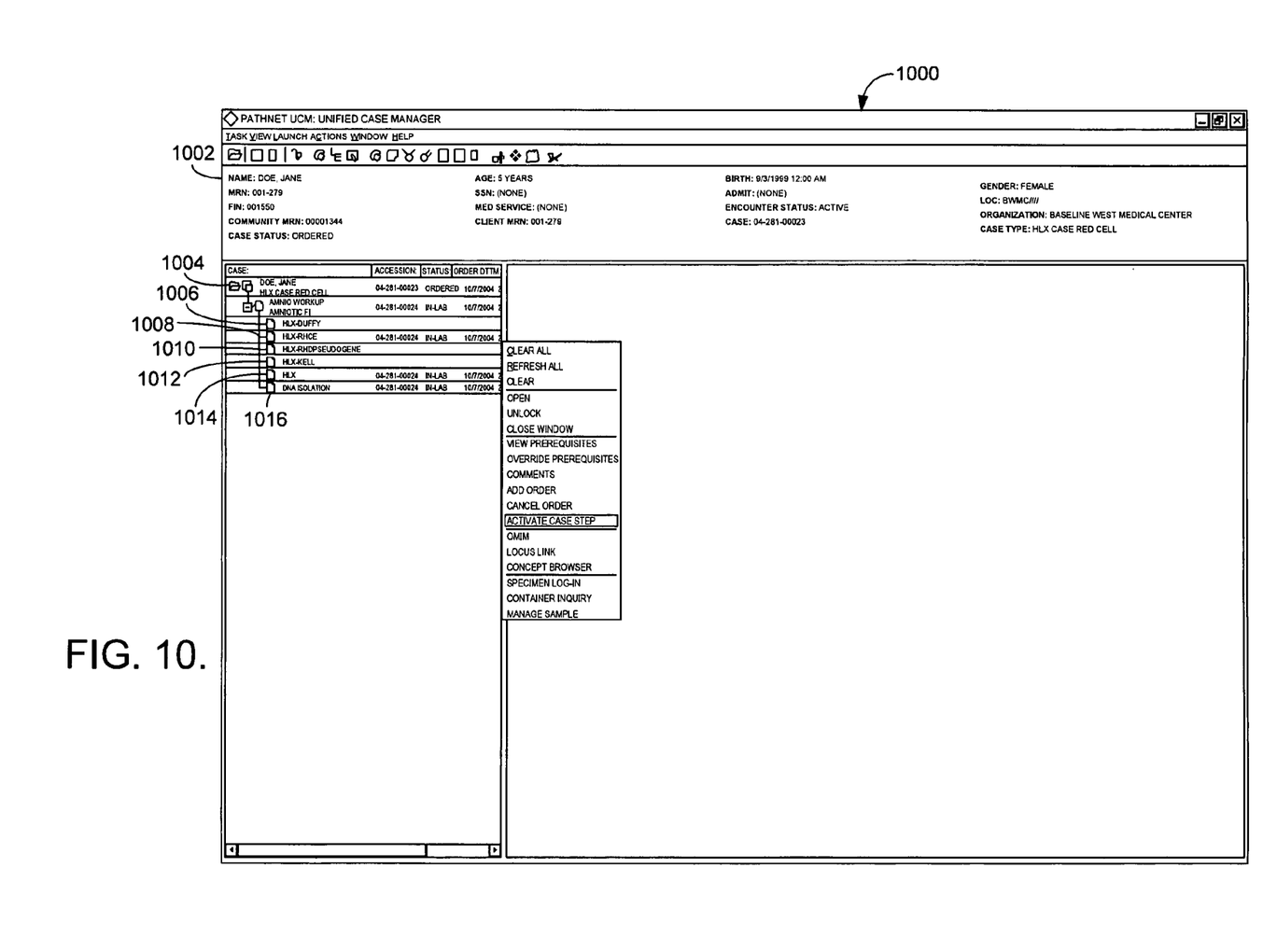
FIG. 10 is a screen displaying how an optional order may be activated after an order set has been placed in accordance with an embodiment of the present invention.

Referring next to FIG. 10, an exemplary screen 1000 displaying activated and non-activated optional orders is shown. In this example, the screen is displayed to a second user, such as a laboratory scientist or technologist. The screen includes the order set list 1004 for fictitious patient Jane Doe 1002. As can be seen in the order set list 1004, optional orders HLX RHCE 1008 and HLX-RHE 1014 were selected and placed by a first user. The status of optional orders 1008 and 1014 is that the orders are in the laboratory awaiting completion. The required order for DNA Isolation 1016 has also been placed for the order set for the patient.

Optional orders HLX-Duffy 1006 and HLX-Kell 1012 were displayed to a first user in FIG. 9, but were not selected and placed. As such, these optional orders may still be selected and placed by the second user. These optional orders may also be selected and placed by any other user with appropriate access and authorization. The optional order HLX RHD-Pseudogene 1010 has been designated to be displayed only to the second user, such as a laboratory scientist of technologist. As such, optional order 1010 was not displayed to the first user as shown in FIG. 9. Optional order 1010 is shown as being selected and activated by the second user.

Figure 11:
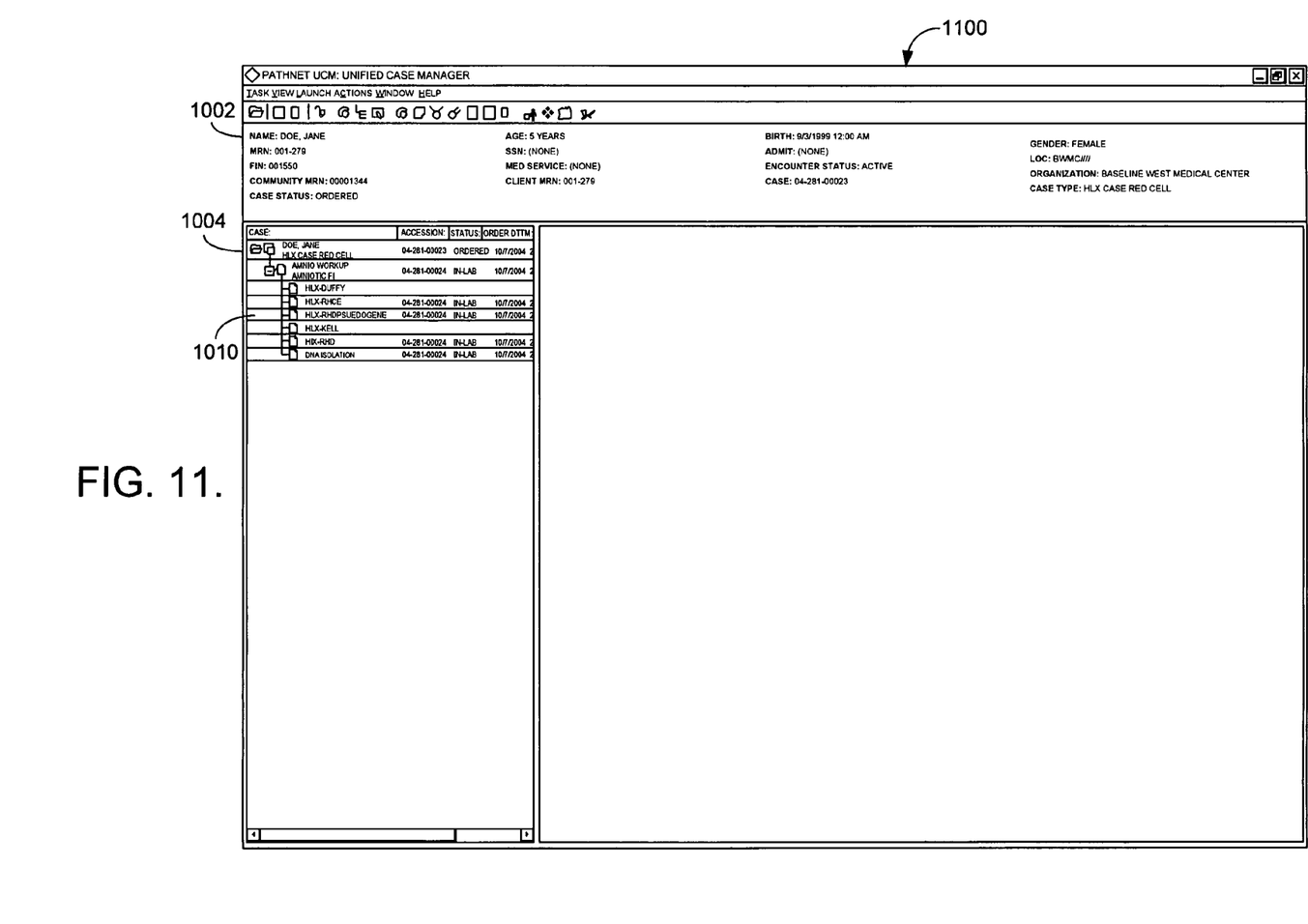
FIG. 11 is a screen displaying an optional order after it has been activated in accordance with an embodiment of the present invention.

Referring next to FIG. 11, a screen 1100 displaying activated and non-activated optional orders is shown. In this example, the screen shows optional orders for an orders set activated by either a first and second user, and required orders activated for the order set that are for fictitious patient Jane Doe 1002. However, in FIG. 10, optional order 1010 selected and activated by a second user in FIG. 11 is shown as having been placed and in the laboratory for completion.

By way of example, an order set may be for testing red cell antigen gene systems within a molecular diagnostic laboratory. The specific red cell antigen gene systems that can be tested for are RH C, RH D, Kell, RHD Pseudogene and Duffy. The actual gene system(s) that needs to be tested is dependent on the particular patient being tested. Thus, an order set has been built such that the red cell antigen gene system orders are optional orders within the order set. When the order set is selected, a user is prompted to identify which optional orders should be included when the order set is placed. The selected optional orders are activated and the order set is placed in the system. After the order set has been placed, during the clinical analysis of a case, a user may determine that activating an optional order not previously activated is appropriate. The user may right click on the representation of the order, select "activate order" and the order becomes active triggering related billing and workload events triggered within the system.

The present invention has been described in relation to particular embodiments, which are intended in all respects to illustrate rather than restrict. Alternative embodiments will become apparent to those skilled in the art that do not depart from its scope. Many alternative embodiments exist, but are not included because of the nature of this invention. A skilled programmer may develop alternative means for implementing the aforementioned improvements without departing from the scope of the present invention.

It will be understood that certain features and sub-combinations of utility may be employed without reference to features and sub-combinations and are contemplated within the scope of the claims. Furthermore, the steps performed need not be performed in the order described.

The invention claimed is:

1. A method in a computerized environment for placing selectable orders for an order set for a patient, the method comprising:

receiving a request to display an order set for a patient, wherein the order set comprises a first, second and third selectable orders, as well as required orders, and wherein the required orders are not selectable and are placed by default when the order set is placed;

determining at the same time, by a first computing process, that the third selectable order is not to be displayed until the required orders and at least one of the first selectable order and the second selectable order have been placed in the system, wherein placing the order in the system makes the order active in the system triggering related billing and workload events within the system;

displaying the first and second selectable orders and not the third selectable order;

receiving selection of the first selectable order to be placed for the order set and determining that the second selectable order was not selected to be placed;

placing by a second computing process, the required orders and the first selectable order selected for the order set establishing a formal presence of the required orders and the first selectable order in a workflow and triggering billing-related and clinical events; and displaying, after the required orders and the first selectable order have been placed, the second selectable order which was not selected to be placed and the third selectable order, wherein displaying the second selectable order again provides another opportunity for the second selectable order to be selected and placed, and wherein the third selectable order is displayed for the first time only after the required orders and at least one of the first selectable order and the second selectable order have been placed, and wherein the first and second computing processes are performed by one or more computing devices.

2. The method of claim 1, further comprising:
determining to automatically place the first selectable order for the order set.

3. The method of claim 2, further comprising: placing the first selectable order for the order set.

4. The method of claim 1, wherein the order set comprises selectable orders for red cell antigen gene systems.

5. A system having one or more computing devices with a processor coupled to a memory in a computerized environment for placing selectable orders for an order set for a patient, the system comprising:

a first receiving component receiving a request to display an order set for a patient, wherein the order set comprises a first, second and third selectable order, as well as required orders, and wherein the required orders are not selectable and are placed by default when the order set is placed;

a first determining component performed by a first computing process determining the first, second and third selectable orders for the order set, and the required orders, the third selectable order being designated not to be displayed until after at least one of the first selectable order, the second selectable order, and the required orders have been placed, wherein placing the order in the system makes the order active in the system triggering related billing and workload events within the system;

a displaying component displaying the first and second selectable orders and not the third selectable order;

a second receiving component receiving a selection of the first selectable order to be placed for the order set, wherein the second selectable order was not selected to be placed;

an ordering component performed by a second computing process placing the required orders and the first selectable order selected for the order set establishing a formal presence of the required orders and the first selectable order in a workflow and triggering billing-related and clinical events; and a displaying component displaying, after the required orders and the first selectable order have been placed, the second selectable order which was not selected to be placed the third selectable order, wherein displaying the second selectable order again provides another opportunity for the second selectable order to be selected and placed, and wherein the third selectable order is displayed for the first time only after the required orders and at least one of the first selectable order and the second selectable order have been placed, and wherein the first and second computing processes are performed by the one or more computing devices.

6. The system of claim 5, further comprising:
a fourth computing process for determining to automatically place the first selectable order for the order set.

7. The system of claim 6, wherein the second computing process places the first selectable order.

* * * * *